United States Patent [19]

Horiba et al.

[11] 4,352,020
[45] Sep. 28, 1982

[54] METHOD AND APPARATUS FOR EXAMINING A SUBJECT

[75] Inventors: Isao Horiba, Nagoya; Shigenobu Yanaka, Kashiwa; Yasuo Kuwabara, Kashiwa; Kouichi Koike, Kashiwa, all of Japan

[73] Assignee: Hitachi Medical Corporation, Tokyo, Japan

[21] Appl. No.: 109,088

[22] Filed: Jan. 2, 1980

[30] Foreign Application Priority Data

Jan. 11, 1979 [JP] Japan .................................. 54-989

[51] Int. Cl.$^3$ .................................................. A61B 6/00
[52] U.S. Cl. .................................... 378/18; 250/252.1
[58] Field of Search ............................ 250/445 T, 252

[56] References Cited

U.S. PATENT DOCUMENTS

| | | | |
|---|---|---|---|
| 3,881,110 | 4/1975 | Hounsfield et al. | 250/445 T |
| 4,028,554 | 6/1977 | Hounsfield | 250/445 T |
| 4,149,247 | 4/1979 | Pavkovich et al. | 250/445 T |
| 4,225,789 | 9/1980 | Albrecht | 250/445 T |
| 4,233,507 | 11/1980 | Volz | 250/252 |

*Primary Examiner*—Alfred E. Smith
*Assistant Examiner*—T. N. Grigsby

*Attorney, Agent, or Firm*—Gerald J. Ferguson, Jr.; Joseph J. Baker

[57] ABSTRACT

In the X-ray CT system, the X-ray detectors vary in output characteristics such as linearity, directivity and radiation quality from one detector to another. To make compensations for such irregularities, a plurality of phantoms of different absorption is prepared in the CT system according to the present invention. Namely, this plurality of phantoms is set one by one in the measuring space in the same manner as in the examination of an examinee or subject to be examined; the coefficient of X-ray absorption is determined for each of these phantoms. Further, theoretical values of absorption for each phantom are compared to the actual absorption measurements on each phantom to provide an absorption error value for each detector at differing absorption levels. The actual subject absorption value for each detector is used to pick the two error values closest to the actual value. The two error values are interpolated or extrapolated to find an error value for correcting the actual absorption value. The above method steps are advantageously implemented by one or more digital computers. The corrected subject absorption values are provided to a conventional image reconstruction device to provide the desired X-ray video image.

12 Claims, 23 Drawing Figures

|  | a | b | c | d | e | f |
|---|---|---|---|---|---|---|
| CHANNEL 1 → | $d_o(1,a)$ | $d_o(1,b)$ | $d_o(1,c)$ | $d_o(1,d)$ | $d_o(1,e)$ | $d_o(1,f)$ |
| CHANNEL 2 → | $d_o(2,a)$ | $d_o(2,b)$ | $d_o(2,c)$ | $d_o(2,d)$ | $d_o(2,e)$ | $d_o(2,f)$ |
|  | ∫ | ∫ | ∫ | ∫ | ∫ | ∫ |
| CHANNEL k → | $d_o(k,a)$ | $d_o(k,b)$ | $d_o(k,c)$ | $d_o(k,d)$ | $d_o(k,e)$ | $d_o(k,f)$ |
|  | ∫ | ∫ | ∫ | ∫ | ∫ | ∫ |
| CHANNEL ℓ → | $d_o(\ell,a)$ | $d_o(\ell,b)$ | $d_o(\ell,c)$ | $d_o(\ell,d)$ | $d_o(\ell,e)$ | $d_o(\ell,f)$ |
|  | ∫ | ∫ | ∫ | ∫ | ∫ | ∫ |

FIG.5(A)

|  | a | b | c | d | e | f |
|---|---|---|---|---|---|---|
| CHANNEL 1 → | $d(1,a)$ | $d(1,b)$ | $d(1,c)$ | $d(1,d)$ | $d(1,e)$ | $d(1,f)$ |
| CHANNEL 2 → | $d(2,a)$ | $d(2,b)$ | $d(2,c)$ | $d(2,d)$ | $d(2,e)$ | $d(2,f)$ |
|  | ∫ | ∫ | ∫ | ∫ | ∫ | ∫ |
| CHANNEL k → | $d(k,a)$ | $d(k,b)$ | $d(k,c)$ | $d(k,d)$ | $d(k,e)$ | $d(k,f)$ |
|  | ∫ | ∫ | ∫ | ∫ | ∫ | ∫ |
| CHANNEL ℓ → | $d(\ell,a)$ | $d(\ell,b)$ | $d(\ell,c)$ | $d(\ell,d)$ | $d(\ell,e)$ | $d(\ell,f)$ |
|  | ∫ | ∫ | ∫ | ∫ | ∫ | ∫ |

FIG.5(B)

|  | a | b | c | d | e | f |
|---|---|---|---|---|---|---|
| CHANNEL 1 → | $\delta(1,a)$ | $\delta(1,b)$ | $\delta(1,c)$ | $\delta(1,d)$ | $\delta(1,e)$ | $\delta(1,f)$ |
| CHANNEL 2 → | $\delta(2,a)$ | $\delta(2,b)$ | $\delta(2,c)$ | $\delta(2,d)$ | $\delta(2,e)$ | $\delta(2,f)$ |
|  | ∫ | ∫ | ∫ | ∫ | ∫ | ∫ |
| CHANNEL k → | $\delta(k,a)$ | $\delta(k,b)$ | $\delta(k,c)$ | $\delta(k,d)$ | $\delta(k,e)$ | $\delta(k,f)$ |
|  | ∫ | ∫ | ∫ | ∫ | ∫ | ∫ |
| CHANNEL ℓ → | $\delta(\ell,a)$ | $\delta(\ell,b)$ | $\delta(\ell,c)$ | $\delta(\ell,d)$ | $\delta(\ell,e)$ | $(\ell,f)$ |
|  | ∫ | ∫ | ∫ | ∫ | ∫ | ∫ |

METHOD AND APPARATUS FOR EXAMINING A SUBJECT

BACKGROUND OF THE INVENTION

1. Technical Field

This invention relates to a method and apparatus for examining a subject.

2. Prior Arts

In general, apparatuses for examining portions of a human body for diagnostic purposes suffer more or less from artifacts produced in an obtained tomogram or lowering of resolution due to movements of the subject or movements of internal organs of the subject. To minimize such artifacts or lowering of resolution, it is essential to shorten a measuring time. To this end, there has been proposed a measuring apparatus comprising an X-ray tube for generating a fan beam type X-ray having a given spreading angle and a plurality of X-ray detectors and adapted to make measurement while rotating the X-ray tube and the detectors group around the subject to be examined, keeping a given positional relation therebetween. This type of apparatus can greatly reduce a scanning time as compared with a conventional apparatus which makes a measurement only by traverse and rotation movement.

However, if the detectors of such an apparatus have individual differences in X-ray detecting performance (herein after referred to as an "X-ray detecting characteristic"), there are again caused artifacts or lowering of resolution in an obtained image. In fact, it is reported by papers etc. that a noise due to such differences between individual characteristics of the detectors appears in the form of a ring in an obtained computed tomogram (CT) image. To prevent these phenomena, it is essential that not only each detector have general characteristics as a radiation detector but also it have highly accurate, uniform and stable energy response or characteristics such as sensitivity, offset, linearity, directional characteristic and ray-quality characteristic.

However, in fact, it is quite difficult to prepare such ideal detectors. By this reason, efforts have been made to effectively improve characteristics of the detectors by improving a measuring method. As to uniformalization of sensitivity of the detectors, there has been proposed a method wherein X-rays are preliminarily irradiated before a subject is placed in the machine, the sensitivities of the respective detectors are stored in a memory and measured values obtained upon actual measurement of the subject are divided by the stored sensitivities to make calibration. There has also been proposed a method for eliminating offset errors. This method comprises a step of applying pulsed X-ray just before measurement, a step for storing, into a memory, output values, i.e. offset values of the respective detectors obtained when the X-ray is not applied, namely, during intervals of the pulses, and a step of cancelling outputs of the detectors obtained during the measurement with the stored data of the offset values. According to this method, not only the offset errors can be eliminated but also an influence by variation with time can be reduced.

However, energy response such as linearity, directional characteristic, and ray-quality characteristic inherent of the respective detectors cannot easily be corrected. For example, in a detector comprised of a Xenon gas chamber, a plurality of electrodes are arranged in parallel with each other within a casing, and it has been known that, when the detectors of this type are arranged so as to form a multi-channel detectors group, there are problems such as electric fields of respective electrode ends of the detectors are not uniform, the respective electrodes have delicate differences in their formation and the respective detectors have different insulation resistances. Therefore, it is quite impossible to provide highly uniformalized characteristics of the detectors, such as linearities, directional characteristic, and ray-quality characteristic. The differences in characteristics between individual detectors can be regarded as errors. To correct such errors of the respective detectors, there has been proposed the following method: a plurality of phantoms having uniform beam passage lengths and uniform absorptivities are placed by turns in the course of an X-ray beams (a measuring path); the X-ray is irradiated onto the respective phantoms, a penetrated X-ray obtained through the phantoms is detected by a multi-channel type detectors group; error values due to non-uniformity in output levels of the detectors are stored so as to correspond to the respective detectors and the respective output levels; the error values preliminarily measured are used for calibration in measurement of a subject by applying the error values to the outputs of the detectors obtained in the subject measurement according to the levels thereof. In accordance with this method, as the absorption of the uniform phantom increases, the ray quality of the X-ray incident upon the detectors becomes harder. Therefore, if the subject and an X-ray absorption spectrum of the uniform phantom are made of like materials, the non-uniformity in linearity and ray-quality characteristic can be highly improved. However, this method cannot correct errors in directional characteristic of the detectors. More specifically, when fan beam type X-rays produced from an X-ray tube are irradiated onto the subject, there occurs scattering of the X-ray within the subject so that not only a main X-ray but a scattering X-ray produced in the subject is detected in the respective detectors. If there is no difference or variability in directional characteristics among the individual detectors, the scattering X-ray only imparts spacially biases to the respective detectors in a low frequency range. On the other hand, if there are differences or variabilities in directional characteristics, bias components imparted to the respective detectors produce errors in outputs of the detectors related to the contour of the subject when the subject is actually made to undergo a measurement. Therefore, the errors due to the scattering X-ray cannot be eliminated by such correcting means as mentioned above. A method for correcting errors due to such a scattering X-ray and ray quality is described herebelow. A phantom is first prepared which has an X-ray absorbing characteristic similar to that of a subject and a contour similar to that of the subject and is made of a material uniform at least within a region to be observed. Images of the phantoms are obtained according to the size and contour of subjects, and subtraction is carried out between the image of the subject and the phantom image. This method performs substracting operation between the data corresponding to the absorption value obtained by measuring the phantom and the data corresponding to the absorption value obtained by measuring the subject so that errors due to the ray-quality characteristic and scattering X-ray can be equivalently reduced. In this method, however, fitness of a material, size and configuration of the phantom to the subject is an important factor of reducing errors.

Therefore, in actual application of the method, it is required to prepare various phantoms adapted for subjects to be measured and to sample various error data thereof. In addition, an obtained image is effective only for a portion of the phantom where an absorptivity distribution is uniform. A portion out of the range where the absorptivity distribution is uniform produces artifacts. As a result, an effective region becomes narrow in the measurement and it is required to set the subject in the narrowed effective region for every measurement.

SUMMARY OF THE INVENTION

It is therefore an object of the present invention to provide a method and apparatus for examining a subject, which is capable of eliminating differences or variabilities in output characteristics of respective detectors, such as linearity, directional characteristics and ray quality characteristics, with high accuracy.

A first aspect of the present invention is to provide a method for examining a subject, which comprises obtaining differences between theoretical absorption values of a phantom and actual absorption values obtained by measuring the phantom mounted on a measuring path, performing comparison operation between actual absorption values of a subject obtained by measuring the subject set on the measuring path and the actual absorption values of the phantom, searching for the corresponding differences based on the result of the comparison operation and automatically making interpolation or extrapolation for the absorption value of the subject based on the searched difference.

A second aspect of the present invention is to provide an apparatus for examining a subject which is capable of carrying out the aforesaid method.

A third aspect of the present invention is to provide an examining method and apparatus wherein an arithmetic operation for obtaining differences, a comparison operation, searching operation, interpolation or extrapolation and calibration are all carried out by a digital computer.

A fourth aspect of the present invention is to provide an examining method and apparatus wherein a multichannel type detector system is used as a detecting system.

A fifth aspect of the present invention is to provide an examining method and apparatus wherein phantom elements of various configurations may be used.

A sixth aspect of the present invention is to provide a computed tomography (CT) apparatus or an X-ray apparatus utilizing the aforesaid interpolating or extrapolating method and means.

BRIEF DESCRIPTION OF THE DRAWINGS

FIGS. 2 (A), (B), (C), (D) and (E) are perspective views of phantoms employable in the present invention, respectively;

FIG. 4 and FIGS. 5 (A) and (B) are data formations;

FIGS. 7 (A) and (B) are explanatory views of the principle of the present invention, illustrating interpolation thereof;

PREFERRED EMBODIMENT OF THE INVENTION

Referring now to the drawings, there is illustrated a preferred form of computed tomography (CT) apparatus in accordance with the present invention.

Figure 1:
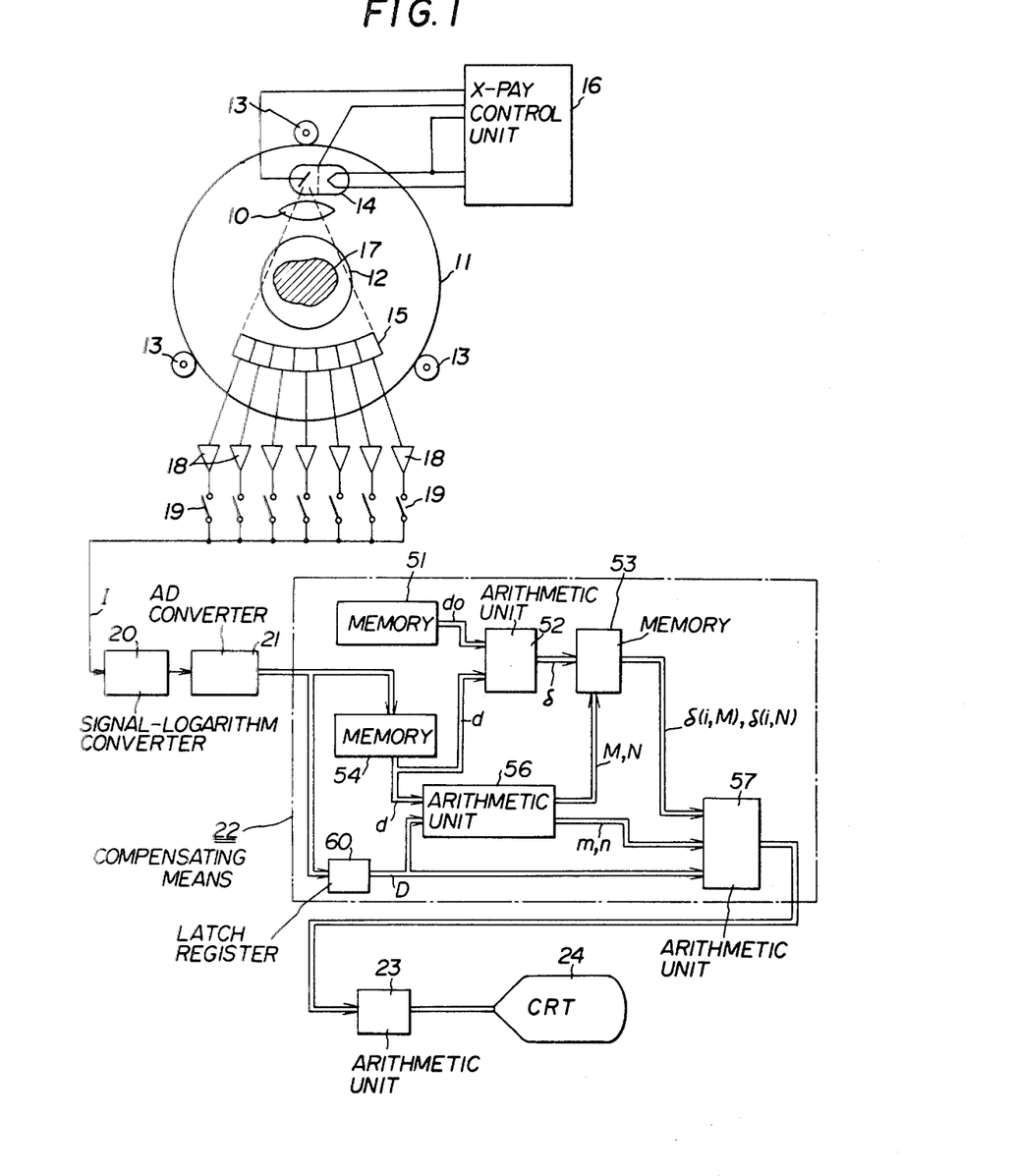
FIG. 1 is a diagrammatic view of one embodiment of the present invention.

In FIG. 1, a rotating frame 11 is formed in a disc-like shape and has a measurement zone 12 therein. A subject 17 to be examined is placed within the measurement zone 12. A periphery of the rotary frame 11 is supported by rollers 13 provided on a base table (not shown) and is adapted to rotate on the rollers 13. An X-ray source 14 includes an X-ray tube and collimator (not shown in FIG. 1). An X-ray produced from the X-ray tube is expanded by the collimator into a fan beam type X-ray 10 having a given extent. A multi-channel type X-ray detector group 15 comprises a plurality of detectors, each of which is formed of a xenon gas chamber including a plurality of X-ray detecting elements. There are provided detecting elements as many as they can cover the extent of the X-ray. The X-ray source 14 and the detector group 15 are supported by the rotating frame 11 and adapted to be rotated according to rotation of the rotating frame 11, keeping a predetermined positional relationship between the X-ray source 14 and the detector group 15. The rotation of the rotating frame 11 is attained for example by an electric motor in cooperation with a sprocket and a chain (not shown).

An X-ray control unit 16 having a high voltage generating function and an X-ray control function is adapted to generate pulsed fan beam type X-ray having a given duration upon every rotation by a given rotational angle, e.g. by 10°. The subject 17 is supported on a bed within the measurement zone 12 between the X-ray source 14 and the detector group 15 and located relative to the X-ray so that a section thereof to be examined may coincide with a section through which the X-ray penetrates. Each of the detectors of the X-ray detector group 15 is adapted to receive directly or indirectly, the X-ray irradiated from the X-ray source 14 after every rotation of the predetermined angle. Where the detector or detectors receive the X-ray indirectly, they detect the X-ray attenuated by the subject and output electrical signals proportional to amounts of the detected X-ray. Integrating amplifiers 18 are adapted to integrate, within a given period of time, the electrical signals outputted from the detectors upon every X-ray irradiation. However, the integrating amplifier 18 is preliminarily reset before it receives an electrical signal accompanying a further X-ray irradiation. Analog switch means 19 are adapted to sequentially select the outputs I of the respective integrating amplifiers 18 and input them into a signal-logarithm converter 20. The signal-logarithm converter 20 is adapted to perform an operation of −log I with respect to the output value I of each integrating amplifier and convert the output of the respective integrating amplifier into an output corresponding to an X-ray absorption value. This output is led to an analog-to-digital converter (hereinafter referred to as "A–D converter") 21, where it is converted into a digital signal. An output of the A–D converter 21 is corrected by correcting means 22 as will be mentioned in detail later and imputted into an arithmetic unit 23 having an image reconstructing function. The arithmetic unit 23 is of a known means for image reconstruction in the art and adapted to perform a required operation based on the output signals from the respective detectors to calculate an image of distribution of X-ray absorption and to display the measured image on CRT provided in an indicator 24 including a video digital-to-analog converter.

In the apparatus of the present invention, correction values of output data for the respective detectors are obtained prior to initiating an actual measurement of the subject and output signals from the respective detectors obtained upon such an actual measurement are calibrated by the corresponding correction values, respectively, so as to eliminate individual differences in linearities, directional characteristic, and ray-quality characteristic of the output characteristics of the respective detectors. To this end, the aforesaid correcting means 22 is provided.

The correction values are determined by using a plurality of phantom elements b, c, d, e and f as illustrated in FIG. 2 (A), (B), (C), (D) and (E), respectively. The elements are each formed in a columnar or disc-like shape and made of a material having an X-ray absorptivity substantially the same as that of the subject, e.g. a polyethylene resin or an acrylic resin. Each element may be a hollow member made of a synthetic resin and containing therein water or physiologic saline. The phantom elements b, c, d, e and f have, as illustrated in FIG. 2, different X-ray passage lengths $l_1$, $l_2$, $l_3$, $l_4$ and $l_5$, respectively. In other words, the phantom elements b, c, d, e and f have different diameters. The phantom elements b, c, d, e and f are disposed by turns so that the center axes thereof may be coaxial with a rotation center axis of the X-ray source 14 and the detector group 15. Thus, the detectors can output different levels of X-ray absorption depending on the respective phantom elements.

Figure 3:
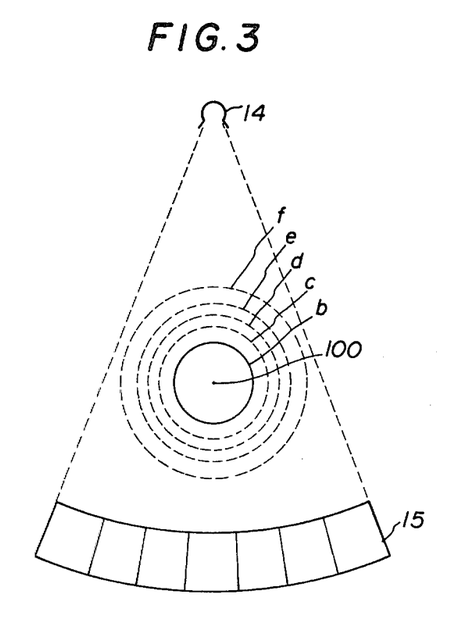
FIG. 3 is a diagrammatic view showing a part of the examining procedure in accordance with the present invention.

It should be noted that as shown in FIG. 3, the plurality of phantom elements is set one by one in such a manner that the disk surface forming the circumference of each phantom element coincides with the plane of X-ray scan.

The X-ray absorption measured on each of the phantom involves the difference in linearity, directivity and radiation quality peculiar to each detector. The aspect of this X-ray absorption will be explained in the following:

As the X-rays irradiated to each phantom are attenuated within the phantom and its intensity becomes low, the portion of lower energy of the specific energy spectrum distribution is selectively absorbed, and the energy spectrum distribution is biased to the higher-energy portion. This is the so-called "phenomenon of X-ray hardening." In this phenomenon, the greater the X-ray absorbing and penetrating thickness, namely, the diameter, the more heavily the energy spectrum distribution is biased to the higher energy with the result that among phantoms composed of a same material, one will possibly be evaluated to be lower in coefficient of X-ray absorption than another of which size, however, is greater than the former. The "phenomenon of X-ray hardening" upon which the X-ray absorption greatly depends is well known as a basic aspect of the X-ray absorption. This is disclosed in the publication "Text for Persons in Charge of Radiology," (1975, pp. 32–34, Japanese Society of Non-Destructive Inspection, incorporated association).

Further, X-rays irradiating the phantom scatter within it. This scattering is a phenomenon in which the X-rays collide with the electrons in the nucleus composing the phantom so that the X-rays themselves are caused to move in a different direction. Since many X-ray particles are reoriented in various directions at this time, X-rays generally seem to be scattered. This phenomenon of scattering is also well known as Compton effect and Thomson scattering; the probability of this scattering is closely related with the energy of X-rays. Generally, the Compton scattering occurs when the X-ray energy is 100 keV to 10 MeV, while the Thomson scattering tends to frequently occur when the energy of X-rays is about 100 keV. More particularly, in the X-ray spectrum used in the X-ray CT, the X-ray energies with which these phenomena of scattering occur are relatively high. Accordingly, these phenomena of scattering involved in the phenomenon of X-ray hardening, of course, vary depending upon the diameter of phantom.

While non-scattered X-rays travel in a same or almost same direction, the scattered X-rays take different directions of travel. When only the scattered X-rays are taken up in question, the phantom seems to be a plurality of scattered radiation sources (in the same manner as the moon appears to be a separate source of radiation apart from the sun).

Consequently, when X-ray detectors of different or irregular directivities are used to measure a phantom, the scattered X-ray component will be included in the measurements as a specific error of each detector with respect to the non-scattered X-rays. The basic mechanism of these phenomena of scattering is also known widely (refer to the above-mentioned "Text for Persons in Charge of Radiology," pp. 19–21 and pp. 24–30).

The signals including the errors derived from the physical mechanism of X-rays are subject to analog processing such as current-voltage conversion, integration, amplification, etc. in the electric circuit including also the X-ray detectors. These analog circuitry has each a specific linearity; accordingly, the digital values finally obtained are those in which the above-mentioned errors are mixed together.

However, if the shape of phantom and the coefficient of X-ray absorption of its material are known, and when the measuring position for that phantom is determined, it is possible to calculate the X-ray absorption of each X-ray detector under the conditions where none of such errors exists. The values thus calculated may be used to determine the specific error of the CT system.

A data formation and memory operative in the correcting means 22 will be described below.

Figure 4:
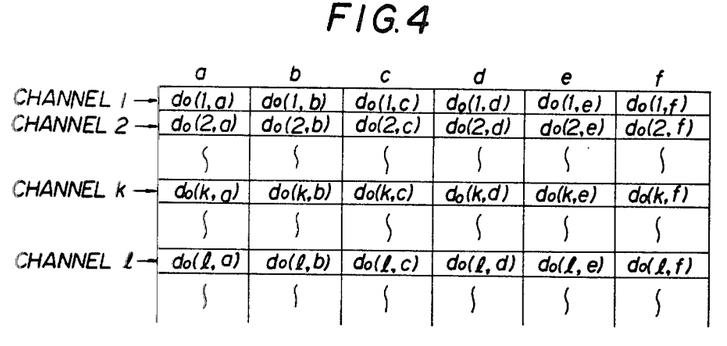
Figure 5A:
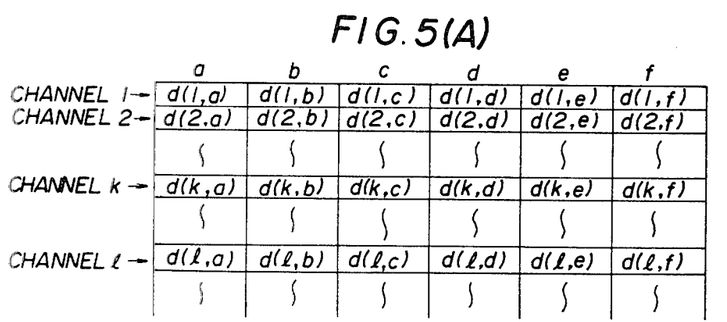
Figure 5B:
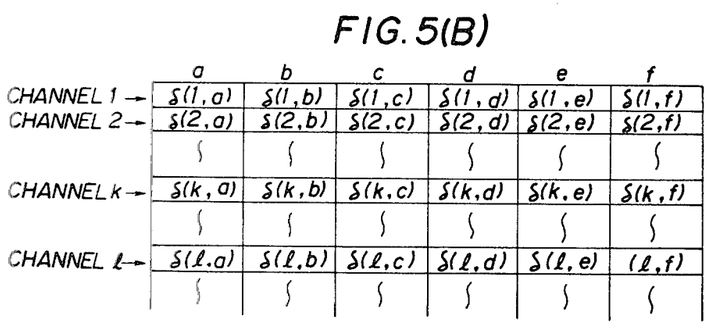

A second memory 51 stores theoretical X-ray absorption values preliminarily calculated based on the above mentioned phantom elements, i.e. X-ray absorption values by channels 1, 2 . . . l . . . calculated in relation with the five phantom elements b, c, d, e and f and a case a where no phantom elements is provided as shown in FIG. 4. On the other hand, a first memory 54 stores a measured value d where no element is placed and measured values d where elements b, c, d, e and f are placed respectively, as shown in FIG. 5 (A). An arithmetic unit 52 performs arithmetic operation to obtain error values $\delta = d_O - d$ by channels between the calculated data $d_O$ stored in the memory 51 and the measured data d stored in the memory 54 respectively. A memory 53 stores the data of the error values $\delta$ of the respective detector channels as shown in FIG. 5 (B).

Arithmetic unit 52 and memory 53 comprise a first arithmetic means for computing and storing error values.

A general operation of the embodiment illustrated in FIG. 1 will now be described.

Prior to measurement of the subject, errors of detector system from the detectors 15 to the A-D converter 21 are measured. These errors correspond to the aforesaid error values $\delta$. Under a condition that no phantom is mounted, i.e. under a condition that no phantom element is placed between the X-ray source 14 and the detector group 15, X'-rays are produced. X-ray absorption values are outputted from the detectors of the respective channels and the values are stored sequentially in the memory 54 through a signal-logarithm converter 20 and the A-D converter 21. The detected data obtained by any one detector channel i is hereinafter expressed as d (i, a). Subsequently, the phantom element b is mounted on the apparatus so that the center axis of the phantom element b may be positioned at the rotational center of the rotating frame 11, namely, the rotational center of the X-ray source 14 and the detector group 15, and X-ray is irradiated under such a condition. The outputs are then stored in the memory 54 as shown in FIG. 5 (A). Similarly, X-ray is sequentially irradiated onto the phantom elements c, d, e and f, and the outputs are stored in the memory 54. The detectors output the X-ray absorption values d upon X-ray irradiation, respectively. The detected data for the respective phantom elements obtained by any one detector channel i are hereinafter expressed as d (i, b), d (i, c), d (i, d), d (i, e) and D (i, f), respectively, as shown in FIG. 5 (A).

On the other hands, the second memory 51 preliminarily stores the data of the theoretical X-ray absorption values $d_O$ for the respective detectors, calculated based on the respective absorbers as shown in FIG. 4. These data are obtained by calculation from the known shapes and X-ray absorption distribution of the phantom elements. The data for any one detector i are expressed as $d_O$ (i, a), $d_O$ (i, b), $d_O$ (i, c), $d_O$ (i, d), $d_O$ (i, e) and $d_O$ (i, f). The arithmetic unit 52 performs an arithmetic operation to obtain the error values by channels between the data $d_O$ stored in the memory 51 and the measured data d of the phantom elements. These are expressed by:

$$(i, a) = d_O (i, a) - d (i, a)$$

$$(i, b) = d_O (i, b) - d (i, b)$$

$$(i, c) = d_O (i, c) - d (i, c)$$

$$(i, d) = d_O (i, d) - d (i, d)$$

$$(i, e) = d_O (i, e) - d (i, e)$$

$$(i, f) = d_O (i, f) - d (i, f) \quad (1)$$

wherein $d_O$ (i, a) is a value obtained under the condition where no phantom element is mounted and $d_O$ (i, a) = 0. The error values $\delta$ are obtained by channels and stored in the memory 53 as shown in FIG. 5 (B).

Figure 6:
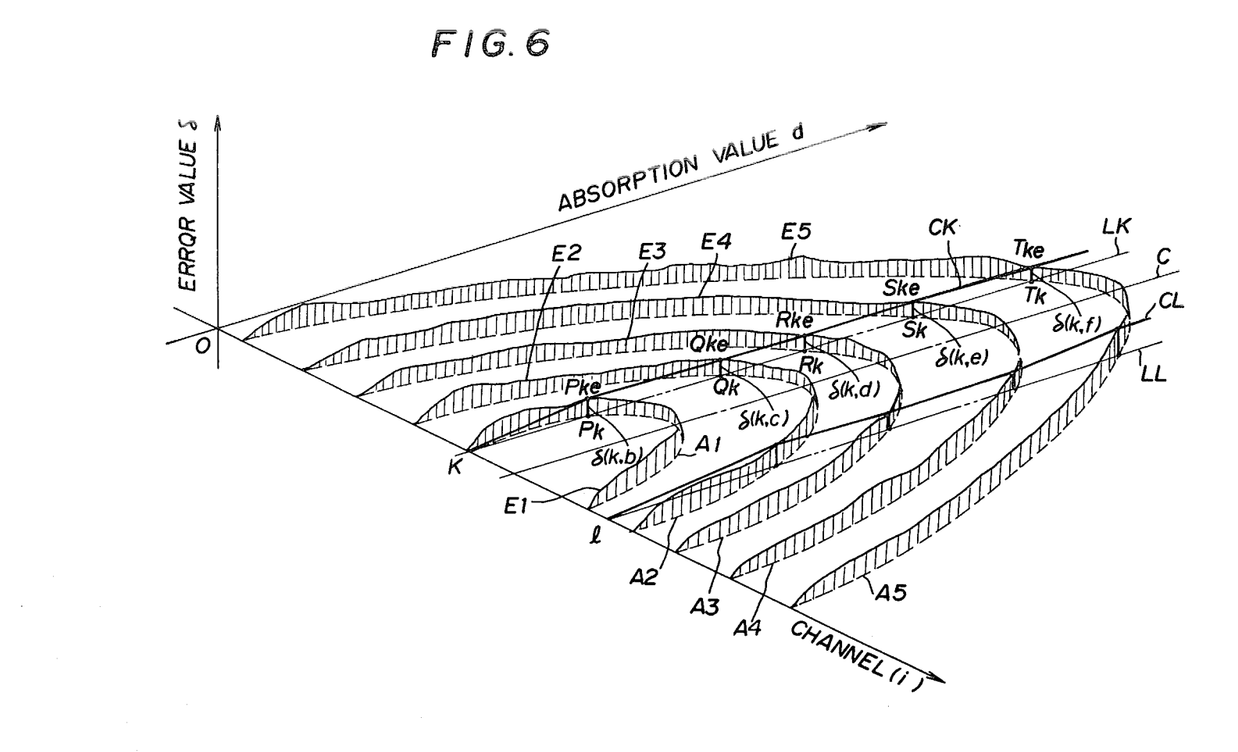
FIG. 6 is an explanatory view of the principle of the present invention.

FIG. 6 shows relationships between the X-ray absorption values d obtained by the measurement of the phantom elements for the respective detection channels and the error values $\delta$. In the figure, the error values $\delta$ are expressed in an ordinate perpendicular to a plane containing the detector channels i and the X-ray absorption values d. The X-ray absorption values measured in relation with the respective phantom elements b, c, d, e and f are shown by five curves $A_1$, $A_2$, $A_3$, $A_4$ and $A_5$ (hereinafter referred to as "absorption curves") obtained in the form of waved curves around the rotation center axis C of the rotating frame in proportion with the diameters $l_1$, $l_2$, $l_3$, $l_4$ and $l_5$ of the respective phantom elements. In the state a where no phantom element is set, the absorption value d is zero and does not appear in the figure. The error values with respect to the respective absorption values are obtained by curves $E_1$, $E_2$, $E_3$, $E_4$ and $E_5$ (hereinafter referred to as "error curves") superposed on the respective absorption curves. Now, the figure is discussed more particularly referring to the channels k and l. The error values at the detector channel k are specified as follows. Intersections of straight lines LK drawn between the absorption values of the respective phantom elements at the channel k and the absorption curves $A_1$, $A_2$, $A_3$, $A_4$ and $A_5$ of the respective phantom elements are indicated by Pk, Qk, Rk, Sk and Tk, respectively. Points on the error curves which correspond to the intersections Pk, Qk, Rk, Sk and Tk are indicated by Pke, Qke, Rke, Ske and Tke, respectively. Distances between the respective intersections and the corresponding points are error values $\delta$. In the figure, the error values $\delta$ are indicated as $\delta(k, b)$, $\delta(k, c)$, $\delta(k, d)$, $\delta(k, e)$ and $\delta(k, f)$ for the respective phantom elements. A curve obtained by plotting the five points Pke, Qke, Rke, Ske and Tke is a correction curve CK for the detector channel k. Correction curves can be similarly obtained for the remaining channels, respectively. In this connection it is to be noted that the number of the intersections between the absorption curves and the straight lines connecting the absorption values differ depending on the channels carrying out detection. For example, at the channel l, the absorption curve $A_1$ does not appear so that a straight line LL drawn between the absorption values of the respective phantom elements c, d, e and f intersect the absorption curves $A_2$, $A_3$, $A_4$ and $A_5$ at four points. In this case, a correction curve is indicated by CL.

Figure 7A:
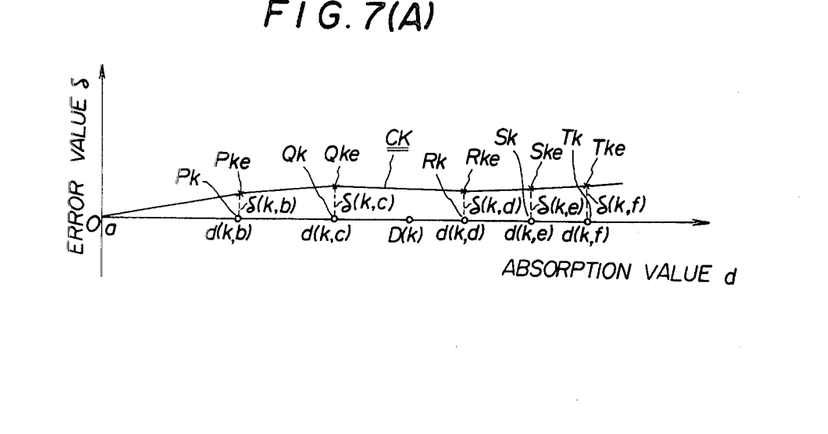
Figure 7B:
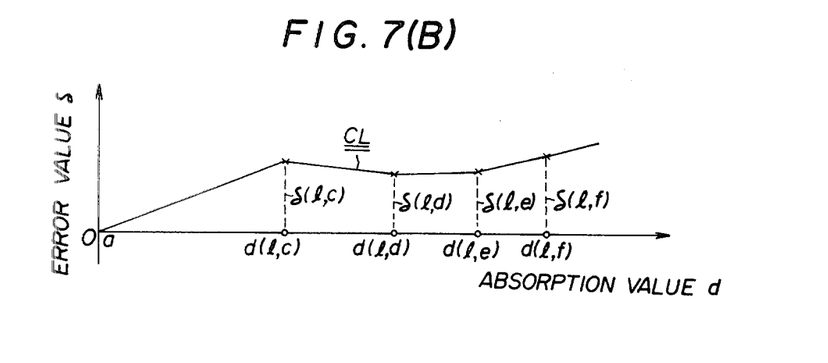

FIG. 7 (A) shows the correction curve CK for the k channel and FIG. 7 (B) shows the correction curve CL for the l channel. These correction curves correspond to sections taken along lines perpendicular to the abscissa i of FIG. 6. As to the correction curve CK, the error values $\delta(k, b)$, $\delta(k, c)$, $\delta(k, d)$, $\delta(k, e)$ and $\delta(k, f)$ are calculated according to the equations (1). Similarly, as to the correction curve CL, the error values $\delta(l, c)$, $\delta(l, d)$, $\delta(l, e)$ and $\delta(l, f)$ are calculated according to the equations (1). The absorption values d and the error values $\delta$ by channels are stored in the memories 54 and 53, respectively, according to the respective tables of FIGS. 5 (A) and 5 (B).

In the apparatus of the present invention, an absorption values d corresponding to the detected data obtained by measurement of the subject are searched for referring to the table of FIG. 5 (A) and linear interpolation for error values are made by using adjacent two error values δ found from the table of FIG. 5 (B) so as to correct the data.

When the subject 17 in FIG. 1 is subjected to a measurement, the detectors 15 produce output signals upon X-ray irradiation onto the subject 17. The output signals are selected by the analog switch means 19 and the detected data D of the detectors selected by the analog switch means 19 are stored by channels in a latch register 60 through the signal-logarithm converter 20 and the A-D converter 21.

A second arithmetic means 56 receives, as inputs, the detected data D of the respective detector channels outputted from the latch register 60 and the measured data d stored in the memory 54, compares the two data, and obtain a corresponding error parameter according to the result of the comparison. More specifically, the arithmetic unit 56 performs an arithmetic operation to obtain a difference between an X-ray absorption value D(i) obtained by the measurement of the subject at the detector channel i and two adjacent X-ray absorption values d (i, M) and d (i, N) which are close to the absorption value D(i) and stored in the memory 54 and outputs parameters m and n. These may be expressed by:

$$m = D(i) - d(i, M)$$

$$n = d(i, N) - D(i)$$

where $d(i, M) \leq D(i) < d(i, N)$. This operation is more specifically explained referring to the k channel in FIG. 7 (A). The absorption value D of the subject 17 is now assumed to be an absorption value D (k) located between the measured absorption values of the phantom elements c and d. In this case the two adjacent values close to the value D (k) are the absorption values of the phantom elements c and d and there can be obtained relations of M=c and N=d. Subsequently, m and n are obtained from the following equations:

$$m = D(k) - d(k, c)$$

$$n = d(k, d) - D(k)$$

Thus, M, N, m and n are determined. As to the remaining channels, such determination can be carried out in similar manners. The arithmetic unit 56 feeds address in accordance with the data M and N to the memory 53 and reads out error value data δ(i,M) and δ(i,N).

The error value data δ(i,M) and δ(i,N) and the parameters m and n are inputted to an arithmetic unit 57. The arithmetic unit 57 comprises a third arithmetic means which corrects the detected data D (i) according to these inputted data and outputs a corrected signal Dc (i) as follows:

$$Dc(i) = [D(i) + n\delta(i,M) + m\delta(i,N)]/(m+n) \quad (2)$$

The data of the respective detector channels upon measurement of the subject are sequentially corrected in a similar manner and inputted to the arithmetic unit 23 having an image reconstructing function. The arithmetic unit 23 performs image reconstruction by a method known as back projection method and the indicator 24 reproduces the image of the subject reconstructed according to the X-ray absorption distribution of the subject. Since the image reconstructing operation itself is not novel and the image reconstruction can be effected simply by using the corrected data Dc, detailed description is not given here in this respect.

Although the calculation of the linear interpolation according to the equation (2) is shown as an example of methods for obtaining the data Dc in the foregoing embodiment, other interpolation methods may also be employed in the present invention as will be mentioned below.

(1) The linear interpolation can be effected by using a calculation equation other than the equation (2). As a typical example thereof, there can be mentioned an equation where the parameters m and n are replaced with other values.

(2) As examples other than the linear interpolation, there can be mentioned higher order interpolation. In the higher order interpolation, more than two points are employed as different from the linear interpolation.

(2-1) Example of cubic interpolation

Figure 8:
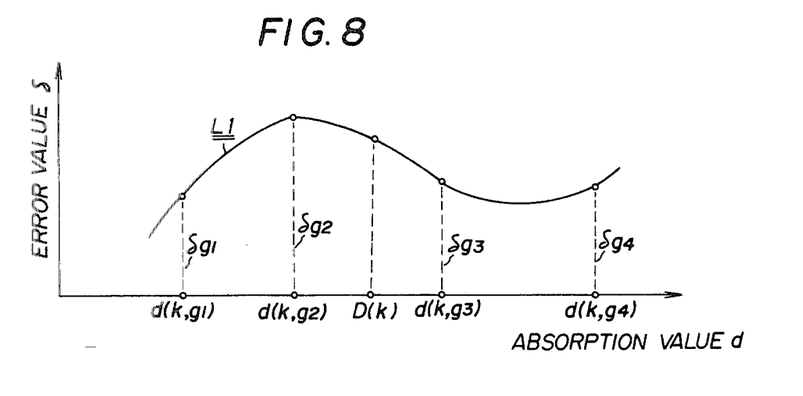
FIGS. 8 and 9 are explanatory views illustrating other interpolations of the present invention.

An example of the cubic interpolation for the channel k is illustrated in FIG. 8. As absorption value data, there are employed two abrorption values $d(k,g_1)$ and $d(k,g_2)$ before the absorption value D(k) of the subject, two absorption values $d(k,g_3)$ and $d(k,g_4)$ after the absorption value D(k) and error values $\delta g_1$, $\delta g_2$, $\delta_3$ and $\delta_4$ corresponding to the respective absorption value data. A correction curve $L_1$ is drawn based on the four error values and the four absorption values. Thus, a correction value Dc(k) corresponding to the data D(k) is obtained.

(2-2) Example of biquadratic interpolation

Figure 9:
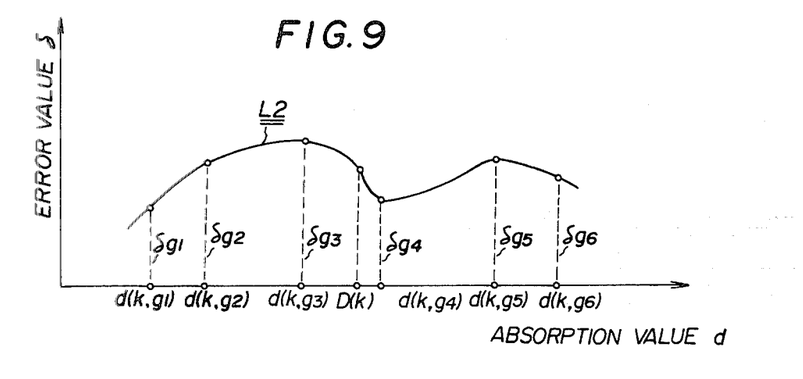

FIG. 9 illustrates an example of the biquadratic interpolation with respect to the channel k. As absorption value data, there are employed three absorption value data $d(k,g_1)$, $d(k,g_2)$ and $d(k,g_3)$ and another three absorption value data $d(k,g_4)$, $d(k,g_5)$ and $d(k,g_6)$ before and after the absorption value D(k) respectively and error values $\delta g_1$, $\delta g_2$, $\delta g_3$, $\delta g_4$, $\delta g_5$ and $\delta g_6$. Based on the six error values and the six absorption values, a correction curve $L_2$ is drawn to obtain a correction value Dc(k) corresponding to the data D(k).

(2-3) Example of TRW cubic interpolation

In this example, a TRW cubic equation is employed.

In the foregoing higher order interpolation, it is essential to employ five or more phantom elements to assure high accuracy.

Figure 10:
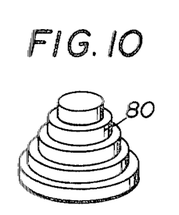
FIGS. 10, 11 and 12 are perspective views of other forms of phantoms employable in the present invention.
Figure 11:
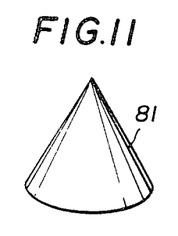
Figure 12:
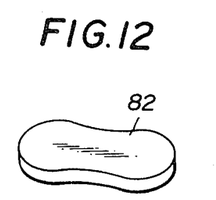

Although five separate columnar or disc shaped elements are used as a phantom in the embodiment as mentioned above, the phantom may be formed in other configurations. As a first example, FIG. 10 illustrates a phantom 80 wherein columnar elements b, c, d, e and f identical with those illustrated in FIG. 2 are coaxially laid upon one another to form an integral structure. As a second example, a conical phantom as illustrated in FIG. 11 is employed. In these examples, the phantoms have a circular measuring section, but the measuring section is not always required to be circular. Therefore, as a third example, there can be mentioned a phantom 82 having a configuration as illustrated in FIG. 12.

Figure 2A:
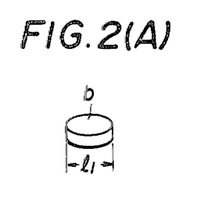
Figure 2B:
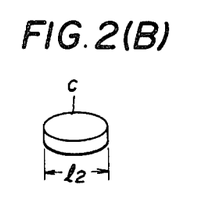
Figure 2C:
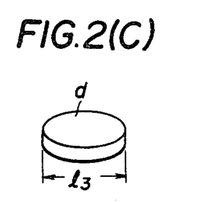
Figure 2D:
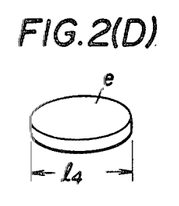
Figure 2E:
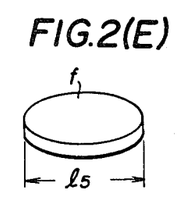
Figure 13:
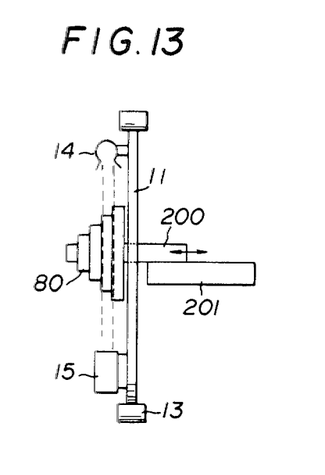
FIG. 13 is a schematic view of one form of examining apparatus according to the present invention which employs the phantom illustrated in FIG. 10.

Actual applications of the respective phantoms 80, 81 and 82 will now be explained. FIG. 13 illustrates an application example of the phantom 80. An phantom support member 200 for giving a thrust to the phantom 80 is mounted on a guide member 201. The support member 200 is adapted to make a thrust movement in directions indicated by arrows so that there can be obtained the same effects as attained by loading and unloading each of the separate phantom elements as illustrated in FIG. 2.

Figure 14:
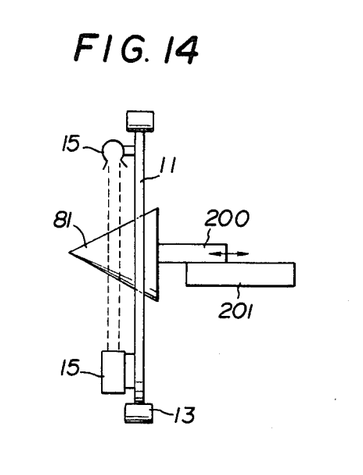
FIG. 14 is a similar schematic view of another form of examining apparatus according to the present invention which employs the phantom illustrated in FIG. 11.
Figure 15:
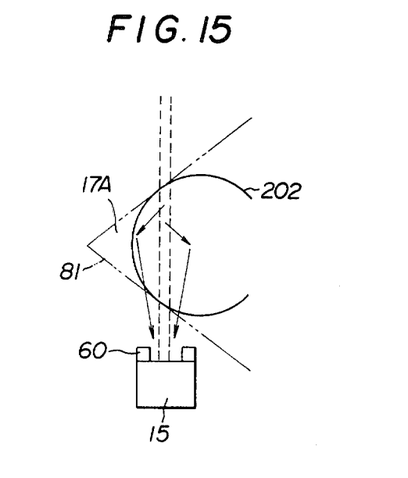
FIG. 15 is an explanatory view showing effects of the apparatus illustrated in FIG. 14.

FIG. 14 illustrates an application example of the phantom 81. The phantom 81 is mounted in the same manner as the phantom 80 in FIG. 13. In this example, the phantom 81 has a continuous curved surface so that desired number of error value measuring points can be provided. Furthermore, since the curved surface of the phantom 81 has a configuration similar to the head of a human body, the phantom 81 is suitable for measurment of a subject such as the head of the human body. Besides, the phantom 81 can provide a high correction effect due to the directional characteristics of the detectors. Stated illustratively, when X-ray is penetrated through the phantom, various scattering rays 202 are produced as illustrated in FIG. 15. The phantom 81 has an effect to make unbalance in flux into the detectors 15 due to such scattering ray 202 analogous to that in the human head 17A. In FIG. 9, numeral 60 designates a collimator.

Figure 16:
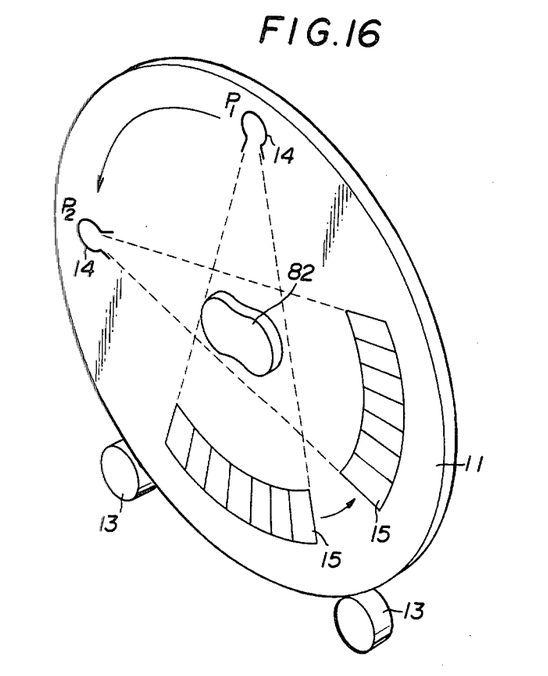
FIG. 16 is a schematic view of a further form of examining apparatus according to the present invention which employs the phantom illustrated in FIG. 12.

FIG. 18 illustrates an application example of the phantom 82. Measurement of the phantom 82 is performed at different angles at positions $P_1$ and $P_2$. This phantom 82 may be employed when the subject is the chest, the abdomen, the loins, etc.

The present invention provides other various modes for carrying out the invention as given below.

(1) Although the latch register 60 is employed in the embodiment of FIG. 1 to temporarily store the data by channels therein, allowing interpolation or extrapolation in real time, another memory may be employed in place of the latch register, which memory stores, by channels, absorption data obtained from the phantom. The data stored in the memory may be utilized to attain similar interpolation or extrapolation considering error values.

Figure 17:
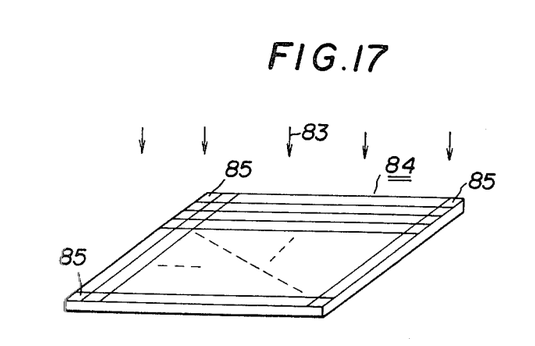
FIG. 17 is one form of solid image storage panel (device).

(2) The present invenntion may have applications other than the CT apparatus, for example, an X-ray apparatus. The general X-ray apparatus well known is adapted to pick up a penetrated image onto a photographic film, but recently a multi-channel type detectors group such as a solid image storage panel (device) has been employed in place of the photographic film in the X-ray apparatus. The image storage pannel is illustrated in perspective view in FIG. 17. In the figure, the image storage pannel 84 has detecting elements 85 formed in matrix. Each of the detecting elements 85 is adapted to detect, penetrated X-ray. Electrodes for the respective detecting elements 85 are omitted in the figure. As mentioned above, this invention is applicable to this type of X-ray apparatus. In this case, a cone beam type X-ray is employed.

(3) The correcting means 22 of the present invention may be a digital computer. Further alternatively, the arithmetic unit 23 and the correcting means 22 may be replaced with at least one digital computer. Although the signal-logarithm converter 20 is provided before the A-D converter 21 in the embodiment of FIG. 1, the signal-logarithm converting operation may be carried out after the A-D conversion and accordingly may be carried out by a treatment within the digital computer.

(4) Since the X-ray irradiated from the X-ray source 14 changes with time, a reference X-ray detecting means may be provided between the X-ray source 14 and the opening portion 12 of the rotating frame 11. A detected signal from the reference X-ray detecting means is inputted through an integrator to the signal-logarithm converter 20 together with the outputs from the switch means 19. In this case, the signal-logarithm converter 20 performs correction of changes in X-ray with time based on the inputs thereto. This mode may be employed in combination with the mode described in (3) above.

(5) The mode of (3) may be applied to a CT apparatus. In other words, there may be provided a CT apparatus wherein a cone beam type X-ray is employed instead of a fan beam type X-ray. In this case, the image storage pannel 84 is employed as the detectors group 15. In this connection, it is to be noted that the modes (3) and (5) each have not a linear formation but a planar formation after the detectors group 15 so as to accommodate the formation to the cone beam type X-ray.

(6) The phantoms illustrated in FIGS. 2, 10, 11 and 12 may be suitably combined with each other in use according to necessity.

(7) Although interpolation is made to estimate missing values in the foregoing embodiment, extrapolation may be employed by suitably selecting a range of known values.

As mentioned above, in accordance with the present invention, hardening in beam quality caused within the phantom and effects of the linearity and scattering ray onto the absorption value can be collectively measured and calibrated as errors by channels. Furthermore, an excellent image quality can be assured irrespective of the size and configuration of a subject.

We claim:

1. A tomography system, comprising an X-ray source and X-ray detectors disposed opposite to said source, an examinee to be placed in the measuring path interposed between said X-ray source and detectors; an emission of X-rays from said source, the X-rays, having penetrated through the examinee, being detected by said X-ray detectors to obtain measurements of X-ray absorption through the examinee from the detected values, which system is characterized by:

a plurality of disk-shaped standard phantoms of different radii which are set one by one in the examinee measuring position in said measuring path in such a manner that the disk surface forming the circumference of each phantom coincides with the plane of X-ray scan;

first memory to store X-ray absorption, for each standard phantom, obtained from the values, detected by said detectors, of X-ray having penetrated through said standard phantom after irradiated from said source to said phantom;

second memory to store theoretical X-ray absorption, for each standard phantom, obtained based on said each of the standard phantoms;

X-ray absorption stored in said first memory and the theoretical X-ray absorption being used as data for compensation of the measurements of X-ray absorption from said examinee.

2. A tomography system as set forth in claim 1, in which said each disk-shaped standard phantom is formed by a disk-like container made of synthetic resin in which physiological salt solution is sealed.

3. A tomography system as set forth in claim 2, in which said disk-like container is made of polyethylene resin.

4. A tomography system as set forth in claim 3, in which said disk-like container is made of acrylic resin.

5. A tomography system as set forth in any one of claims 2, 3 and 4, in which said plurality of disk-shaped standard phantoms are integrally and concentrically formed with each other.

6. A tomography system, as set forth in claim 1, in which said disk-shaped standard phantom is composed of a disk-like container made of synthetic resin, in which water is sealed.

7. A tomography system as set forth in claim 6, in which said disk-like container is made of polyethylene resin.

8. A tomography system as set forth in claim 6, in which said disk-like container is made of acrylic resin.

9. A tomography system as set forth in any one of claims 6, 7 and 8, in which said plurality of disk-shaped standard phantoms are integrally and concentrically formed with each other.

10. A tomography system for providing an improved reconstructed video image, said system including an X-ray source, a group of X-ray detectors, each detector aligned to provide absorption values along a respective channel between said X-ray source and each of said detectors, a measuring zone located substantially between said X-ray source and said group of detectors, means for permitting said source and detector group to rotate around said measuring zone, and means for image reconstruction and display based upon absorption values, said tomography system further comprising:

phantom means for providing at least two different known amounts of absorption between said source and said detector group, said phantom means including means for controllably selecting among said different known amounts of absorption;

first memory means for storing absorption values from said detector group with said phantom means providing said at least two different amounts of absorption for each channel;

second memory means for storing theoretical absorption values for said at least two different amounts of absorption;

first arithmetic means, responsive to said first memory means and said second memory means, for computing and storing specific absorption value errors at said at least two different amounts of absorption for each channel;

second arithmetic means, responsive to said first memory means and to actual subject absorption values, for providing, for each channel, outputs indicative of the difference between said actual patient absorption values and two of the actual phantom absorption values stored in said first memory means which are closest to said actual patient absorption value for that channel, said second arithmetic means providing an absorption address output to said specific value errors stored in said first arithmetic means which specific value errors correspond to the errors at said two absorption values which are closest to said actual patient absorption data for that channel; and third arithmetic means, responsive to said actual patient absorption value, said two different indicative outputs of said second arithmetic means, and said specific absorption value errors stored in said first arithmetic means, for providing a corrected subject absorption value output for each of said channels to said image reconstruction and display means.

11. The tomography system in accordance with claim 10, wherein said phantom means comprises a plurality of disk-shaped elements of differing diameters.

12. The tomography system according to claim 10, wherein said third arithmetic means provides said corrected subject absorption value in accordance with the following formula:

$$Dc(i) = [D(i) + n\delta(i,M) + m\delta(i,N)]/(m+n)$$

where $Dc(i)$ = corrected absorption value for channel i;

$D(i)$ = actual subject absorption value for channel i;

$m = D(i) - d(i,M)$ with $d(i,M)$ equal to the actual phantom absorption value which is one of two values that are adjacent $D(i)$ and is located at absorption address M;

$n = d(i,N) - D(i)$ with $d(i,N)$ equal to the actual phantom absorption value which is the other of two values that are adjacent $D(i)$ and is located at absorption address N;

$\delta(i,M)$ = error between theoretical and actual absorption values for phantom having an absorption address value M;

$\delta(i,N)$ = error between theoretical and actual absorption value for phantom having an absorption address value N.

* * * * *